United States Patent [19]

Raghuprasad

[11] Patent Number: 4,576,157

[45] Date of Patent: Mar. 18, 1986

[54] ORAL INHALATION APPARATUS

[76] Inventor: Puthalath K. Raghuprasad, 315 N. Golder, Suite A, Odessa, Tex. 79761

[21] Appl. No.: 544,777

[22] Filed: Oct. 24, 1983

[51] Int. Cl.$^4$ ............................................. A61M 15/00
[52] U.S. Cl. ............................ 128/200.23; 128/203.15; 604/58; 222/402.13
[58] Field of Search ...................... 128/200.23, 203.15; 604/58; 222/402.13, 61

[56] References Cited

U.S. PATENT DOCUMENTS

| | | | |
|---|---|---|---|
| 3,157,179 | 11/1964 | Paullus et al. | 128/200.23 |
| 3,187,748 | 6/1965 | Mitchell et al. | 128/200.23 |
| 3,302,834 | 2/1967 | Alsop | 222/162 |
| 3,404,681 | 10/1968 | Fowler | 128/173 |
| 3,456,644 | 7/1969 | Thiel | 128/173 |
| 3,456,645 | 7/1969 | Brock | 128/173 |
| 3,456,646 | 7/1969 | Phillips et al. | 128/173 |
| 3,565,070 | 2/1971 | Hanson et al. | 128/173 |
| 3,605,738 | 9/1971 | Ciranna | 128/173 |
| 3,636,949 | 1/1972 | Kropp | 128/173 |
| 3,732,964 | 5/1973 | Thompson et al. | 128/173 |
| 3,789,843 | 2/1974 | Armstrong et al. | 128/173 |
| 3,814,297 | 6/1974 | Warren | 128/208 |
| 3,826,413 | 7/1974 | Warren | 128/173 |

FOREIGN PATENT DOCUMENTS 555681 11/1974 Switzerland .................. 128/200.23

*Primary Examiner*—Henry J. Recla
*Attorney, Agent, or Firm*—Marcus L. Bates

[57] ABSTRACT

An oral inhalation apparatus having a flow responsive valve associated therewith for controlling the flow of medication from an aerosol canister into one's lungs. An aerosol canister is received within a housing and the outlet thereof is received within a tubular passageway so that when the canister is pressed down respective to the housing, the valve means associated with the canister is moved to the open position. A second valve means is positioned downstream of the canister valve means and is spring loaded into the normally closed position. When the patient places a mouthpiece of the apparatus within his mouth and inhales, a sail device is moved downstream in reaction to the flow of inhaled air, thereby moving the second valve to the open position which releases medication into the mouthpiece. Consequently, when the patient initially depresses the canister, thereby opening the canister valve, there is no flow from the canister. However, when the patient inhales, the sail actuated valve is moved to the open position and medication is released into the mouthpiece and flows into the mouth, throat, and lungs. At the end of the inhalation, the sail returns the valve to the closed position. Therefore, medication can flow from the canister only during the time when one is properly inhaling. Another embodiment of the invention is provided for the ease of use by severely ill asthmatics, wherein a movable rubber ring is used to adjust the tension in the spring loading mechanism. When the rubber band is moved down sufficiently, upon depressing the canister, a slow, controlled flow of the medication aerosol issues without need for deep inhalation by the patient. Where such a device is deemed adequate, one can eliminate the sail altogether.

13 Claims, 12 Drawing Figures

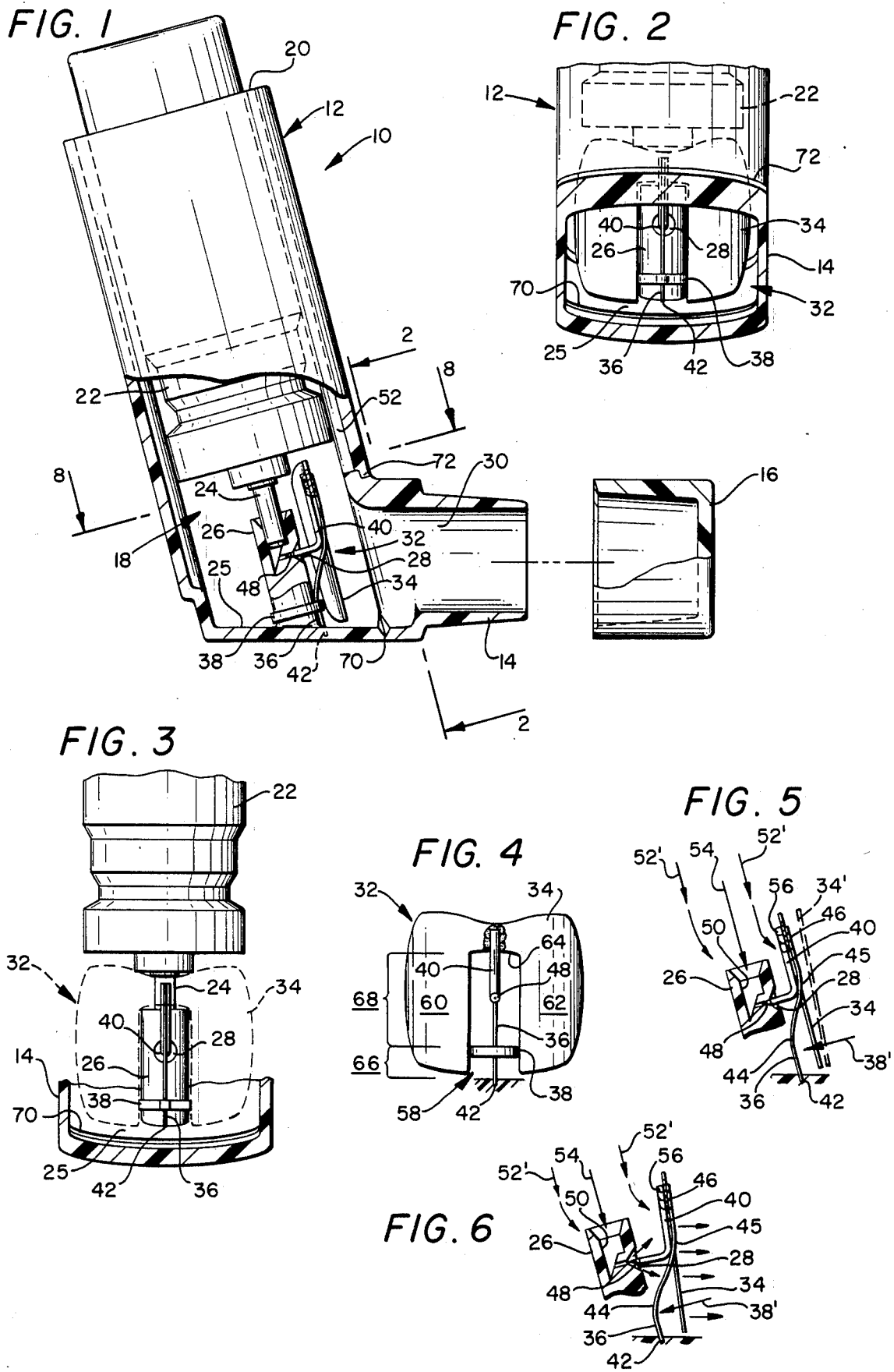

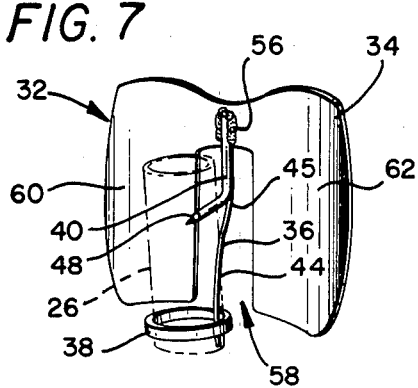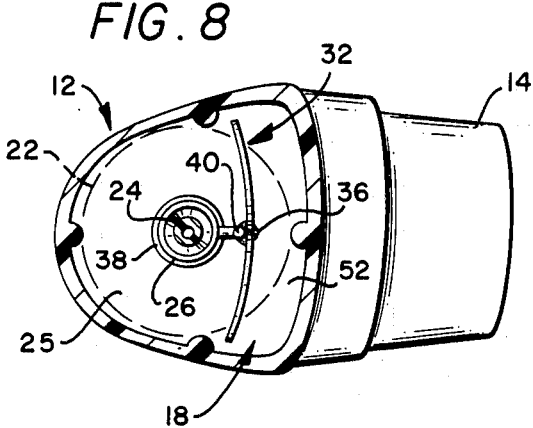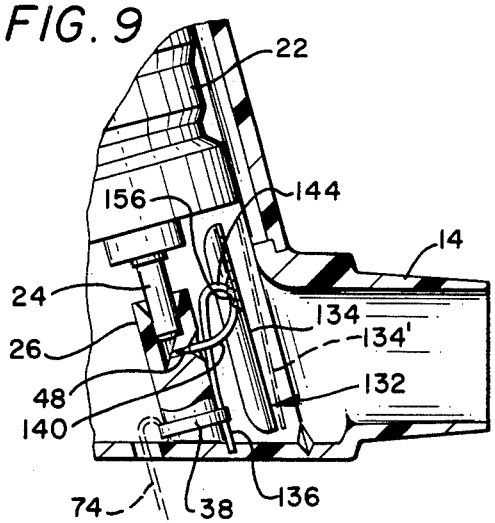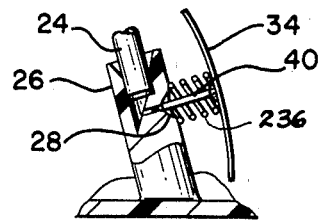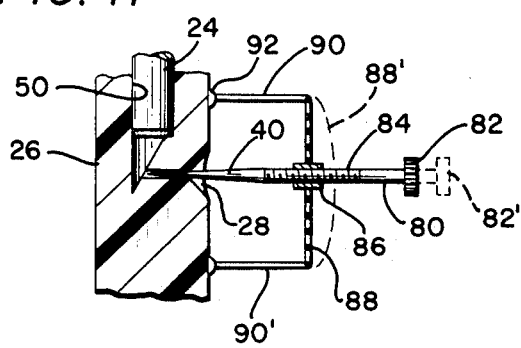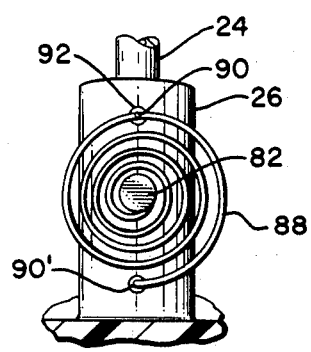

ORAL INHALATION APPARATUS

BACKGROUND OF THE INVENTION

Oral inhalation devices for dispensing medication from an aerosol canister into one's lungs are known to those skilled in the art as evidenced by the patents to:

| | | | |
|---|---|---|---|
| Thompson, et al | 3,732,864 | Kropp | 3,636,949 |
| Armstrong, et al | 3,789,843 | Warren | 3,814,297 |
| Warren | 3,826,413 | Ciranna | 3,605,738 |
| Hanson et al | 3,565,070 | Brock | 3,456,645 |
| Phillips et al | 3,456,646 | Thiel | 3,456,644 |
| Alsop | 3,302,834 | Fowler | 3,404,681 |
| Mitchell et al | 3,187,748 | Paullus et al | 3,157,179 |

Inhalers of the type referred to above are provided with a mouthpiece arranged laterally respective to a housing within which a canister of medication is contained. Theoretically, the mouthpiece is received within one's mouth, and the canister is then depressed, thereby opening the canister valve and releasing the medication into the mouthpiece where the medication is admixed with air and flows into one's lungs. The timed sequence of depressing the canister and deeply inhaling through the apparatus is difficult for the average patient to achieve and consequently, the patient often fails to receive the proper dosage of medication deep down within his lungs.

Often the patient will depress the canister prior to inhaling thus releasing the drug too early for adequate transport to the small airways; or, otherwise, the patient perhaps will depress the canister halfway through the inhalation. In any event, this lack of synchronization between the patient's breathing cycle and the canister movement usually results in only 7–13% of the desired medication properly reaching the lungs.

Others have recognized this problem of synchronization between the patient and the inhaler device and have suggested the use of various different, complex, and expensive flow responsive valve means, as evidenced by some of the above listed patents. The present invention represents a giant step forward in the art for the reason that it provides a relatively inexpensive pressure responsive inhaler device which throttles flow from a canister into one's lungs in a new and unobvious manner.

It would therefore be desirable to have made available an inexpensive, dependable, pressure differential actuated valve means which controls the flow of medication into an oral inhaler mouthpiece so that the medication is dispensed during the entire inhalation, with the opening of the valve occurring substantially at the beginning of the inhaled breath and the closing of the valve occurring substantially at the end of the inhaled breath. Moreover, it would be desirable for the valve means to open and close while air is flowing through the inhaler device and into the patient's mouth, so that there is a minimum loss of medication at the beginning and end of the inhaled breath. Apparatus which achieves these desired results is the subject of the present invention.

SUMMARY OF THE INVENTION

An inhaler apparatus comprising a housing within which a canister of medication is received. A mouthpiece extends from the housing, while ambient air is free to communicate with the housing. The mouthpiece is received within a patient's mouth so that when the patient deeply inhales, medication is released within the housing and is admixed with ambient air, whereupon the mixture then flows through the mouthpiece and into the patient's lungs.

The canister preferably is spaced from the interior housing walls, thereby forming an annular passageway through which air can flow towards the mouthpiece. In the preferred form of the invention, an upright standard provides a passageway through which medication can flow from the canister towards the mouthpiece. The canister outlet is received by the standard, and when the canister is pressed downward, the valve thereof is moved to the open position, thereby communicating the contents of the canister with the passageway of the standard. The passageway of the standard includes an outlet nozzle having a needle valve reciprocatingly associated therewith; so that when the needle valve is moved in a downstream direction, the nozzle is moved to the opened position and medication can flow from the canister into the passageway of the standard, through the nozzle, where air is admixed with the medication. The mixture flows towards the mouthpiece, into the patient's mouth, and then down into his lungs.

A sail is arranged to be moved in response to pressure differential thereacross caused by the flow of the mixture through the housing and mouthpiece. The sail is connected to actuate the needle valve. The needle valve is biased into a normally closed position. When the patient places the mouthpiece into his mouth and presses the canister downward, there is no flow from the nozzle because the needle valve seals the outlet nozzle. The patient then inhales and the pressure differential across the sail moves the needle valve to the opened position whereupon medication flows from the canister interior, into the passageway of the standard, through the nozzle, where the medication is admixed with air. The mixture continues to flow through the mouthpiece, and deep into the patient's lungs. The flow of the mixture continues so long as the pressure differential across the sail is of a magnitude to displace the sail in a downstream direction. At the end of the inhaled breath, the pressure differential across the sail is reduced to a valve which enables the sail to return the nozzle valve to the closed position, thereby shutting off flow from the standard passageway. At this time, assuming a second treatment is not desired, the patient releases the canister which closes the other valve which is associated with the canister outlet.

The canister preferably is a commercially available container of pressurized treatment chemical, and its contents depend upon the drug treatment desired. For example, Schering Corp., Kenilworth, N.J. 07033, markets a canister containing microcrystalline suspension of albuterol in a suitable propellant, dichlorodifluoromethane which delivers the medication in the above described manner. Glaxo Corporations, of Greenford, England also markets a suitable canister containing the above described medication under the trade name of Ventolin. The above described medication is for treatment of spasm of airways, and is one of many examples of various different medication or treatment chemicals which advantageously can be inhaled into the lungs in the above described novel manner.

In another embodiment of the invention, the sail is eliminated, and the actuation of the nozzle valve is pre-adjusted to cause a predetermined flow of medication to occur through the nozzle upon depressing the canister respective to the housing.

Accordingly, a primary object of the present invention is the provision of an inhaler apparatus for use in combination with a canister containing medication which assures that the medication is released into the air flowing into a patient's lungs while the patient is in the act of inhaling.

Another object of this invention is the provision of an improved inhaler apparatus having a pressure responsive valve means which is moved to the open position while a patient is inhaling, and which is moved to the closed position at the end of the inhaled breath, thereby assuring that medication flows from the canister only while the patient is inhaling.

A further object of this invention is to disclose and provide a combination housing, canister of medication, and pressure responsive valve means, wherein, the canister is depressed to thereby open a valve means associated therewith, and thereafter, the patient inhales thereby opening a pressure responsive valve means; and, at the end of the inhaled breath, the pressure responsive valve means is automatically closed, thereby assuring the delivery of medication only while the patient is in the act of inhaling.

A still further object of the present invention is the provision of an inhaler apparatus having a pressure responsive valve means associated therewith which enables the flow of treatment fluid from a canister to occur only while the patient is inhaling.

Another and still further object of the present invention is the provision of a method of translocating treatment chemical, including medication, from a canister by opening a valve means located downstream of the canister a predetermined amount so that medication is released when the canister valve is opened.

These and various other object and advantages of the invention will become readily apparent to those skilled in the art upon reading the following detailed description and claims and by referring to the accompanying drawings.

The above objects are attained in accordance with the present invention by the provision of a method for use with apparatus fabricated in a manner substantially as described in the above abstract and summary.

BRIEF DESCRIPTION OF THE DRAWINGS

FIG. 1 is a side elevational view of the present invention, with some parts thereof being broken away therefrom, and some of the remaining parts thereof being shown in cross-section;

FIG. 2 is a broken, cross-sectional view taken along line 2—2 of FIG. 1;

FIG. 3 is a fragmentary, cross-sectional view, similar in some respects to FIG. 2, with some additional parts being included therewith, and some selected parts being removed therefrom;

FIG. 4 is an isolated, enlarged, detailed, elevational view of part of the apparatus disclosed in FIGS. 1 and 2;

FIG. 5 is a longitudinal, broken, part cross-sectional side view of part of the apparatus disclosed in FIG. 4;

FIG. 6 is an illustration of the apparatus shown in FIG. 5 in an alternate position of operation;

FIG. 7 is a perspective rear view of part of the apparatus seen disclosed in some of the foregoing figures;

FIG. 8 is a cross-sectional view taken along line 8—8 of FIG. 1;

FIG. 9 is a fragmented illustration showing another embodiment of the present invention;

FIG. 10 is a broken, longitudinal, cross-sectional view of still another embodiment of the present invention;

FIG. 11 is a fragmentary, cross-sectional representation of an additional embodiment of the invention; and, FIG. 12 is a broken, part cross-sectional, front view of the apparatus disclosed in FIG. 11.

DETAILED DESCRIPTION OF THE PREFERRED EMBODIMENTS

In the figures of the drawings, there is disclosed an inhaler apparatus 10 made in accordance with the present invention. The apparatus of the invention includes a hollow housing 12 having a mouthpiece 14 laterally arranged respective to the longitudinal axis of the housing. A protective cap 16 is removably received in a slidable manner about the mouthpiece for protecting the mouthpiece from contamination. The housing 12 has a hollow interior as indicated by the arrow at numeral 18. The housing includes an inlet end 20 into which a canister of medication 22 is slidably received.

The canister preferably is an aerosol container within which medication is stored, as for example, microcrystalline suspension of albuterol or beclomethasone in propellants such as trichloromonofluoromethane, dichlorodifluoromethane, and oleic acid. The canister 22 includes a vapor outlet 24 of the standard design having the usual internal normally closed valve means associated therewith.

From the floor 25 of the housing 12, there is rigidly mounted a standpipe 26 having an upper marginal hollow end within which there is received the lower marginal end of the vapor outlet 24, so that when the canister is pressed downwardly towards the standpipe, the valve (not shown) associated with the canister is moved to the open position in the usual manner, and treatment fluid is released to flow towards the nozzle 28 formed in standpipe 26.

The housing forms a passageway 30 which extends from within the hollow interior 18 through the mouthpiece 14. A sail actuated valve assembly, generally indicated by the arrow at numeral 32, controls the flow of medication from the standpipe 26, as will be more fully appreciated later on as the remainder of this disclosure is more fully understood. The sail actuated valve means includes a sail 34 arranged transversely respective to the flow of fluid through the passageway 30. The sail is affixed in mounted relationship respective to a resilient spring mount 36. The spring mount 36 is supported against the standpipe by a biasing means 38. The biasing means 38 preferably is a rubber band approximately 2 mm in thickness and of a diameter to be under tension when it is placed about the standpipe in the illustrated manner of FIGS. 1-3. The sail preferably is made of shim stock which is 0.003 inch thick, 23 mm × 19 mm, and slightly bent towards the standpipe, as illustrated.

The spring mount 36 preferably is made of steel spring alloy wire such as a straight length of stainless steel wire having a diameter of 0.009 inch, for example.

The sail actuated valve means further includes a needle valve 40 connected to be actuated by upstream and downstream movement of the sail 34. The needle valve 40 can be made of steel wire or sturdy plastic material, and preferably has a fixed end directly attached to one face or surface of the sail in the indicated manner illustrated in FIGS. 1, 2, and 4-7.

As best seen illustrated in FIGS. 4 and 5, together with other figures of the drawings, the lower end 42 of the spring mount 36 is mounted in fixed relationship within the floor 25 of the housing 12, thereby leaving a generous medial length of the spring mount free to springingly move away from and towards the standpipe outlet or nozzle 28. The spring mount preferably is normally straight and is deformed into a curve at 44 and 45, due to the biasing force of the rubber band 38. The marginal upper terminal end 46 is affixed to one face of the sail 34.

The needle valve 40 is graduated or reduced in diameter to form a valve element at the marginal free end 48 thereof, and which is made into a suitable complementary size required to cooperate with the standpipe outlet nozzle 28 in a manner to form a flow control valve means in conjunction therewith. As seen illustrated in FIG. 5, the upper interior marginal end of the standpipe is made hollow to provide a passageway 50 for receiving the marginal end 24 of the canister outlet and for receiving medication flowing from the canister 22. Numeral 52 in FIG. 1 illustrates an annular air passageway through which ambient air is available to flow at 52' (FIG. 5) towards the mouthpiece 14 (FIG. 1), and into a patient's lungs (not shown) when the patient deeply inhales. In FIG. 5, numeral 54 indicates the flow of treatment fluid from the interior of the canister and towards the standpipe outlet 28 of the sail valve means.

As seen in FIGS. 4 and 5, together with other figures of the drawings, the fixed end of the needle valve is rigidly affixed to one side of the sail by the illustrated silver solder 56, although other means of attachment, as for example spot welding or cementing, can be advantageously employed in attaching the needle valve to the sail.

The sail preferably is provided with a centrally located cut-out which forms a slot 58 of limited length at the lower major part of the sail. The slot results in the sail having an inverted u-shaped configuration, with each side thereof forming legs 60, and 62. The terminal end 64 of the slot preferably is positioned above the elevation of the nozzle 28 and the needle valve element 48. Access to the biasing means 38 is gained through the slot 58. Biasing means 38, when adjusted through the slot 58, provides means by which the ratio of the lengths of a lower lever arm 66 is changed respective to an upper lever arm 68, seen illustrated in FIG. 4. The biasing means 38 is therefore easily moved up or down the standpipe in a slidable manner by extending a pencil or the like through the slot 58 of the sail and into engagement with the biasing means.

As seen in FIG. 1, a hinge 70 is formed at the floor of the housing while a latch means 72 is formed intermediate the mouthpiece and the main body of the housing so that the latch means can be unfastened, the mouthpiece hingedly rotated away from the main body, thereby gaining access to the sail valve and biasing means 38.

In the embodiment of FIG. 9, wherein similar or like numerals refer to similar or like elements seen illustrated in the preceding figures of the drawings, the needle valve 140 is received within the nozzle 28 of standpipe 26. The needle valve 140 and spring biasing means 136 preferably is a unitary length of spring wire having a medial portion thereof attached to the upstream face of the sail 134. The combination biasing means and needle valve receives a 270° bend, as noted at 136, 144, and 48 in FIG. 9, to increase the bending movement thereof as the sail moves from the illustrated position 134 into the dot-dash position 134'.

In FIG. 10, the standpipe 26 has a nozzle 28 formed at the outlet end thereof, with the standpipe being rigidly affixed to the housing. The sail 34 is supported from the standpipe by spring means 236, which can take on a number of different forms. The relative cross-sectional area of the mouthpiece and the sail can be made of a ratio which achieves any desired throttling ratio. It is possible to fabricate the spring means 236 of various different configuration for varying the biasing force of spring 236.

In operation, the canister 22 is received within the main body of the housing in the illustrated manner of FIG. 1, for example, with the outlet stem 24 thereof being received within the counterbore of the standpipe 26 which forms passageway 50 for flow therethrough of the medication contained within the canister. The canister, when pressed downwardly, causes the stem 24 thereof to move relative to the canister, thereby upsetting the valve associated therewith (not shown) to the open position so that treatment chemical is available within the passageway 50. At this time, the sail valve 32 is in the closed position, noting that the spring mount 36, along with biasing means 38, urges the needle valve 40, 48 into the outlet nozzle 28, thereby providing sufficient obstruction therewithin to prevent any flow whatsoever through the nozzle 28, when properly adjusted.

At this time, the mouthpiece 14 is placed within one's mouth, with the lips sealingly contacting the entire outer peripheral surface area thereof. One next inhales deeply, thereby moving the sail into the dot-dash position 34' seen in FIG. 5, or as seen in FIG. 6, due to the pressure drop effected across the sail 34. At this time, needle valve 40 moves away from nozzle 28, thereby removing the obstruction to flow, whereupon the medication at 50 is immediately available at the nozzle 28. As the patient continues to inhale, the sail 34 remains in the open position 34', and accordingly, medication continues to flow from the interior of canister 22, through the valve stem 24, into passageway 50, through the nozzle 28, through the mouthpiece 14, and into one's lungs. At the end of the inhaled breath, air ceases to flow across the sail, and the absence of the pressure differential thereacross permits the spring biasing force at 36, 38 to return the needle valve 40 into the nozzle 28, thereby precluding further flow of medication from passageway 50, although the valve located in stem 24 may remain in the open position. Assuming that the patient needs only one inhalation per treatment, the canister 22 is next released, thereby moving the canister respective to the valve stem 24, and closing the valve associated therewith. The mouthpiece 14 is replaced onto the protective cap 16, and the inhaler apparatus is stored until needed again.

The flow of medication through nozzle 28 is throttled in accordance with the desired concentration of dosage by moving the rubber band 38 along the standpipe, thereby changing the ratio of the arms 66 and 68. This is accomplished by extending a pencil through the cut-out 58 and into engagement with the rubber band 38; or, alternatively, utilizing a hook 74 in the illustrated manner of FIG. 9. The mouthpiece is advantageously opened to facilitate access to the sail valve device during adjustment thereof.

In the embodiment of FIG. 1, when the rubber band 38 is moved towards its lowest extremity, and the canister 22 is pressed downwardly, it is preferred that the sail valve admit a slight flow at nozzle 28 due to the lower spring forces involved. As the rubber band is moved upwardly along the standpipe, the ratio of the length of arms 66 and 68 decreases towards unity, thereby increasing the spring force, and progressively reducing the metered chemical flowing through the nozzle 28 respective to the pressure differential across the sail. Accordingly, the physician has a means at his disposal for adjusting the dosage received by the individual patient during one inhalation of breath.

In the embodiment of FIG. 1, the needle valve 40 can be attached to the sail 34 as shown, while the spring mount 36 can be removably received within a socket (not shown) attached to the sail, rather than directly attached as shown. This modification permits the spring mount to be attached to the standpipe 26 by rubber band 38, and then the marginal end of the spring mount is received within the sail socket as the free end of the needle valve is received within the nozzle 28.

The sail 34 and needle valve 40, 48 can be a unitary plastic member made by injection molding. In FIGS. 1 and 11, sail valve 32 can be attached to a sleeve, and the sleeve can be telescopingly received about the standpipe 26, thereby enabling the sail valve to be easily retrofitted to a number of housings 12. In this proposed modification, the needle valve is received through an aperture formed laterally through the sleeve wall. The needle valve is received within the nozzle and maintains the sleeve aperture properly aligned with the nozzle.

The present invention precludes the necessity of training the patient to synchronize the opening of the valve at 24 with his breathing. The apparatus of the present invention makes possible an increase in the effective amount of medication reaching the lungs. The apparatus of the present invention is safe to use, extremely inexpensive to manufacture, utilizes many existing prior art components, as for example, the housing 12 and canister 22. More importantly, the present invention provides both method and apparatus by which a patient's lungs can be treated in a manner far superior to the apparatus provided by the prior art. The unexpected improved results achieved herein, along with the simplicity in design, constitutes a novel inhaler which provides unexpected results over the prior art.

In the embodiment disclosed in FIG. 10, the spring means 236 has one terminal end affixed to the standpipe 26 and the other terminal end affixed to the sail 34. When a suitable pressure differential is placed across the sail, the spring 236 is placed in tension as the needle valve is moved downstream by the sail movement.

In the embodiment of FIGS. 11 and 12, a sail can be attached at 82, if desired, to thereby provide still another embodiment of this invention. However, in the specifically illustrated embodiment, there is no sail. The needle valve 40 threadedly engages nut 86. The nut 86 is affixed to spring 88. Knurled adjustment 82 enables the flow through nozzle 28 to be adjusted to any suitable flow.

When the canister 22 is depressed, flow occurs through valve stem 24, into passageway 50, through nozzle 28, and admixes with air. The mixture continues through the mouthpiece and into the patient's lungs. This embodiment of the invention provides a means of throttling the amount of medication admixed with air. It is contemplated to mount the apparatus of FIGS. 10-12 onto an apertured sleeve, and slidably mount the sleeve about the standpipe, rather than directly attach the spring 236 and 88 to the standpipe, thereby enabling the sail valve to be easily installed on a number of different housings 12.

I claim:

1. An inhaler apparatus having a main housing, a canister of treatment fluid removably mounted within said main housing, said canister has an outlet means through which treatment fluid can flow; a valve means, means supporting said valve means within said main housing at a location downstream of said canister, said valve means is connected to the canister outlet means for regulating flow of treatment fluid therefrom;

said valve means includes a valve element, a said means supporting said valve means includes a standpipe attached to said housing, said standpipe having a hollow upper marginal inlet end within which said outlet means of said canister is received, with there being an outlet nozzle communicating with said hollow upper end through which treatment fluid can flow when said valve means is opened; said nozzle being oriented in the direction of said mouthpiece to form a mixture of air and treatment fluid within said mouthpiece; said valve means includes a sail and a needle valve connected to said nozzle for throttling flow through said nozzle in accordance with the magnitude of the pressure drop across the sail, and means associated with said sail for actuating said valve means from a closed to the open position in response to pressure differential effected across said sail; means providing a source of ambient air upstream of said sail;

a mouthpiece connected to said housing at a location downstream of said valve means, said sail being arranged transversely to the direction of flow through said mouthpiece so that when the mouthpiece is placed in one's mouth and a breath of air is taken through said mouthpiece, said sail is forced to move in a downstream direction thereby opening said valve means an amount which is proportional to the pressure differential effected across the sail.

2. The apparatus of claim 1 wherein said means associated with said sail includes a spring mount affixed to said sail and extending into supported relationship respective to said housing so that said spring mount biases said sail towards said nozzle to thereby control flow therethrough.

3. The apparatus of claim 1 wherein said means associated with said sail comprises a spring mount connecting said sail respective to said housing by means of a spring mount; means adjusting the effective length of said spring mount to thereby control the biasing force with which the sail is forced toward said nozzle.

4. The apparatus of claim 3 wherein said spring mount extends into supported relationship respective to said housing so that said spring mount biases said sail towards said nozzle to thereby control flow therethrough;

said means providing a source of ambient air includes a passageway formed between the canister and the housing.

5. An inhaler apparatus of the type having a canister at least partially filled with treatment fluid, said canister includes an outlet through which fluid from the canister can flow, a mouthpiece having a downstream end adapted to be placed within one's mouth so that one can inhale a breath of air therethrough, means by which the upstream end of said mouthpiece is attached to said canister; a pressure actuated valve means supported within said mouthpiece at a location downstream of the canister outlet for controlling flow of treatment fluid therethrough; said valve means having an inlet connected to said canister outlet, an outlet nozzle associated therewith which is oriented in the direction of said mouthpiece to form a mixture of treatment fluid and air within said mouthpiece, a valve seat and a valve element controlling flow from said inlet through said outlet nozzle; said means directly connected to said valve element, a resilient mount means by which said sail means is supported within said mouthpiece and by which said valve element is biased toward said valve seat; means forming an ambient air inlet by which ambient air can flow across said sail means and through the mouthpiece;

whereby when one inhales through said mouthpiece, said sail means moves said valve means to the open position so that treatment fluid is admixed with air and translocated into one's lungs.

6. The apparatus of claim 5 wherein said resilient mount means comprises a spring mount means which supports said sail means and biases said sail means in an upstream direction to thereby maintain said valve means in a normally closed position and to cause said valve means to move to the open position when the sail means is moved in a downstream direction.

7. The apparatus of claim 5 wherein said valve seat is formed in said outlet nozzle and, said valve element extends into said outlet nozzle and is connected to cotrol flow from said canister;

said resilient mount means includes a spring affixed to said sail means and to said valve element and normally biases said sail means and valve element in a direction to cause said valve element to engage said outlet nozzle and preclude flow therefrom when the apparatus is in the standby configuration.

8. The apparatus of claim 5 wherein said sail means is transversely positioned respective to the flow of air through said mouthpiece; said valve element comprising a needle valve element extending from said sail means and into said outlet nozzle for precluding flow therefrom when the sail is in the standby configuration, and for admitting flow therefrom when the sail means is moved in a downstream direction;

said resilient mount means comprising a spring mount having one end affixed to said sail means and the other end affixed to said mouthpiece, said spring mount normally biases said sail means in an upstream direction.

9. The apparatus of claim 8 wherein means are provided by which the effective length of said spring mount is changed to thereby vary the spring force with which the sail means is biased towards the recited upstream direction.

10. The apparatus of claim 5 wherein said sail means is transversely positioned respective to the flow of air through said mouthpiece; said valve element comprising a needle valve element extending from said sail means and into said outlet nozzle for precluding flow therefrom when the sail means is in the standby configuration, and for admitting flow therefrom when the sail means is moved in a downstream direction;

said resilient mount means comprising a spring mount having one end affixed to said sail means and the other end affixed to said mouthpiece, said spring mount normally biases said sail means in an upstream direction; and means are provided by which the effective length of said spring mount is changed to thereby vary the spring force with which the sail means is biased towards the outlet.

11. The apparatus of claim 5 wherein said resilient mount means is an elongated flexible member having one end attached to the mouthpiece and the other end attached to the sail means; said valve means includes a valve element directly affixed to said sail means and positioned to control flow through the valve means in response to movement of the sail means.

12. Method of translocating treatment chemical from a canister into one's lungs an inhaler apparatus of the type having a canister at least partially filled with treatment fluid, said canister includes an outlet through which fluid from the canister can flow, a mouthpiece having a downstream end adapted to be placed within one's mouth so that one can inhale a breath of air therethrough, means by which the upstream end of said mouthpiece is attached to said canister, a pressure actuated valve means supported within said mouthpiece at a location downstream of the canister outlet for controlling flow of treatment fluid therethrough, said valve means having an inlet connected to said canister outlet, an outlet nozzle associated therewith which is oriented in the direction of said mouthpiece to form a mixture of treatment fluid and air within said mouthpiece, a valve seat and a valve element controlling flow from said inlet through said outlet nozzle, said sail means directly connected to said valve element, a resilient mount means by which said sail means is supported within said mouthpiece and by which said valve element is biased toward said valve seat, means forming an ambient air inlet by which ambient air can flow across said sail means and through said mouthpiece, wherein, air is admixed with the treatment chemical and the mixture flows through the mouthpiece into one's mouth and then into one's lungs, according to the steps of:

inhaling through said mouthpiece to move said sail means downstream to the path of air flowing through the mouthpiece;

continuing inhalating through said mouthpiece to create a pressure drop across the sail to move the sail downstream when flow occurs through the mouthpiece;

reciprocatingly moving the needle valve element within the nozzle to thereby throttle flow therethrough in response to the pressure differential caused by inhalation across the sail means;

whereby, when one places the mouthpiece within his mouth and inhales, the sail means moves downstream, thereby opening the valve means and permitting air admixed with the canister contents to flow into one's lungs.

13. The method of claim 12 and further including the steps of:

varying the biasing force of the resilient mount by attaching the resilient mount to structure associated with the mouthpiece with a rubber band.

* * * * *

UNITED STATES PATENT AND TRADEMARK OFFICE
CERTIFICATE OF CORRECTION

PATENT NO. : 4,576,157

DATED : MARCH 18, 1986

INVENTOR(S) : PUTHALATH K. RAGHUPRASAD

It is certified that error appears in the above-identified patent and that said Letters Patent is hereby corrected as shown below:

Column 8, line 12, delete "said valve means includes a valve element, a";

Column 9, line 9, substitute --sail-- for "said", first occurrence.

Signed and Sealed this

First Day of July 1986

[SEAL]

Attest:

DONALD J. QUIGG

Attesting Officer

Commissioner of Patents and Trademarks